United States Patent [19]
Stuart et al.

[11] Patent Number: 5,390,669
[45] Date of Patent: Feb. 21, 1995

[54] DEVICE USING CONNECTOR TUBE TO LOCK INNER CANNULA INSIDE OUTER CANNULA

[75] Inventors: J. Michael Stuart; David Frigger, both of Lake Forest, Calif.

[73] Assignee: Mallinckrodt Medical, Inc., St. Louis, Mo.

[21] Appl. No.: 105,822

[22] Filed: Aug. 9, 1993

[51] Int. Cl.⁶ .................. A61M 16/00; A62B 9/06
[52] U.S. Cl. ................. 128/207.14; 128/911; 128/912; 128/DIG. 26; 128/200.26
[58] Field of Search ......... 128/200.26, 207.14–207.17, 128/911, 912, DIG. 26

[56] References Cited

U.S. PATENT DOCUMENTS

| | | | |
|---|---|---|---|
| 3,169,529 | 2/1965 | Koenig | 128/207.14 |
| 3,225,767 | 12/1965 | Smith | 128/200.26 |
| 4,057,062 | 11/1977 | Lavigne | 128/912 |
| 4,235,229 | 11/1980 | Ranford et al. | 128/912 |
| 4,315,505 | 2/1982 | Crandall et al. | 128/200.26 |
| 4,673,384 | 1/1987 | Schroeder | 128/912 |
| 4,852,563 | 8/1989 | Gross | 128/912 |
| 5,056,515 | 10/1991 | Abel | 128/200.26 |
| 5,067,496 | 11/1991 | Eisele | 128/207.14 |

FOREIGN PATENT DOCUMENTS 183904  7/1966  U.S.S.R. ............ 128/207.14

Primary Examiner—Kimberly L. Asher
Attorney, Agent, or Firm—David A. Hey

[57] ABSTRACT

A tracheostomy device having an inner cannula with a connector head and an outer cannula. The inner cannula is secured within the outer cannula by a locking device having spaced apart, elongated handles that are pivotally mounted on the inner cannula. The handles are spaced such that a connector may be mounted on the connector head, thereby preventing movement of the handles. A method of locking the inner cannula to the outer cannula is also described.

7 Claims, 4 Drawing Sheets

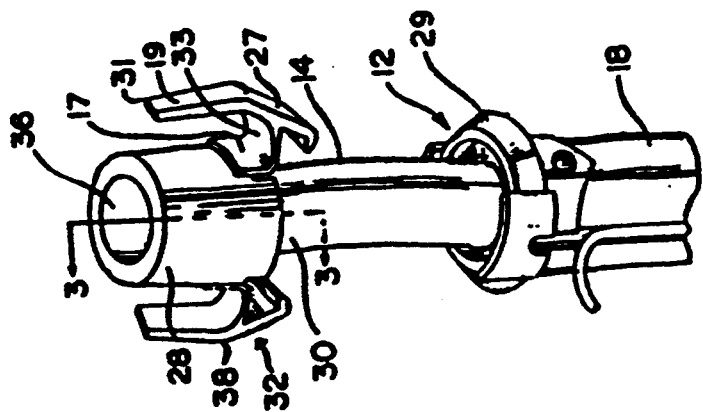
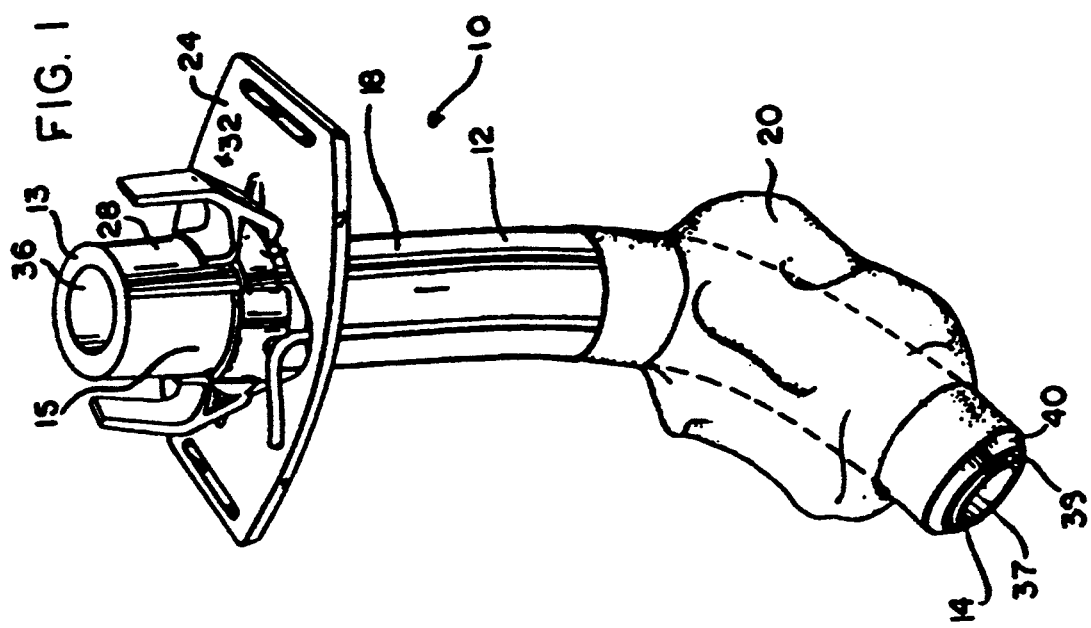

DEVICE USING CONNECTOR TUBE TO LOCK INNER CANNULA INSIDE OUTER CANNULA

BACKGROUND

This invention relates to a tracheostomy device containing outer and inner cannulae and a locking device connecting the inner cannula to the outer cannula and a method of locking the inner cannula to the outer cannula.

DESCRIPTION OF THE PRIOR ART

Tracheostomy tubes are used to assist a patient to breathe. The tube is inserted in a patient's throat through a puncture wound below an obstruction. When in place, the tube provides a direct connection between an oxygen or air source and the trachea.

A common type of tracheostomy tube is equipped with inner and outer cannulae; the inner cannula fitting within the outer cannula. In many tracheostomy tubes with an inner cannula, the inner cannula is provided with a connector head for connection to a ventilator. The inner cannula is removed if obstructed. When the inner cannula is removed, the outer cannula maintains the oxygen or air path to the trachea. To assist in its removal, and to avoid discomfort to the patient, the disposable cannula should be easily detached from the outer cannula. Ease in detachment is particularly important where the patient is connected to a ventilator because it is likely that the patient is unable to breathe on his own while the changeover is accomplished.

Many tubes in the prior art employ manual clamping of the inner cannula to the outer cannula. Crandall, U.S. Pat. No. 4,009,720 employs a device with two clamps having short, cantilevered actuator arms attached to hooks. The clamps are connected to the disposable cannula and the actuator arms are substantially in the same plane as the connection point for the clamps. The clamp is operated by pressing the cantilevered actuator arms, thereby causing the hooks to rotate to an open position against the torque from a flexible hinge. Once the disposable cannula is properly inserted into the outer cannula, pressure is released and the hooks secure the cannulae together. To prevent breakage from an over-extension of the hinge, stops are provided for the clamps. Similar devices are disclosed in U.S. Pat. Nos. Crandall, et al., 3,639,624, Crandall et al., . 4,135,505, Eisele, 5,067,496, and Abel, 5,067,515.

While these clamps adequately secure the inner cannula to the outer cannula, accidental disconnections have occurred because the patient is capable of unfastening the inner cannula while the tracheostomy tube is connected to a ventilator. Such an occurrence is particularly harmful because the airway may be obstructed, presenting the probability of severe injuries or even death. Consequently, a need has developed for a locking system that allows easy detachment of the inner cannula, yet provides security against accidental disconnections when the tracheostomy tube is connected to a ventilator.

THE INVENTION

This invention relates to an improvement in tracheostomy tube assemblies that employs inner and outer cannulae linked by a locking device. The improvement is a locking device for the inner and outer cannulae that prevents the patient from accidentally separating the inner cannula from the outer cannula when it is connected to a ventilator. Part of the inner cannula resides within the outer cannula and the remainder is outside the outer cannula. The inner cannula contains a tapered connector head circumscribing its end that sits outside the outer cannula. The connector head provides the surface for linkage to an air or oxygen source. A readily detachable connector, having a tapered bore that corresponds in mating relationship to the connector head, is attached to the connector head. A locking device, associated with the connector head and the inner cannula, is provided to hold the inner cannula securely in the tracheostomy tube assembly. This device contains a clasp having an elongated handle spaced apart from the connector head and pivotally connected to the inner cannula such that movement of the clasp is permitted towards, and away from, the inner cannula and the tracheostomy tube assembly. The space between the handle portion and the connector head is sufficient for the connector to fit over the connector head so that the connector is between the handle and the connector head and the handle abuts the connector. When the connector is attached to the connector head, the handle is prevented from movement out of its locked position.

The method of the present invention describes a process by which the inner and outer cannulae, as described above, are secured. To begin the process, the distal end of the inner cannula is inserted into the outer cannula, until the locking device, with its elongated handle, contacts the hook securing collar of the outer cannula. At this point, pressure is applied to the elongated handle, compressing it towards the connector head. The clamping device pivot on its flexible hinge, moving it to the open position. Subsequently, the inner cannula is inserted until the connector head contacts the hook securing surface. Pressure is released from the handle. The ventilator connector is affixed to the connector head, occupying the space between the connector head and the handle, thereby completing the process. The handles are now in the locked position. The inner cannula is removed form the outer cannula by reversing the process steps.

Accordingly, it is an object of the present invention to provide a tracheostomy tube assembly in which the outer and inner cannula are securely fastened to one another.

Another object of the present invention is to provide a tracheostomy tube assembly having a locking device that prevents accidental disconnection.

A further object is to provide a locking device that can be easily disconnected, with a minimum of discomfort to the patient.

A still further object of the present invention is to provide an improved method of connecting an inner and outer cannula.

BRIEF DESCRIPTION OF THE DRAWINGS

FIG. 1 is an elevated view of the tracheostomy tube assembly.

FIG. 2 is an elevated view, partially in section, of the inner cannula partially inserted into the outer cannula.

DETAILED DESCRIPTION OF THE INVENTION

Figure 3:
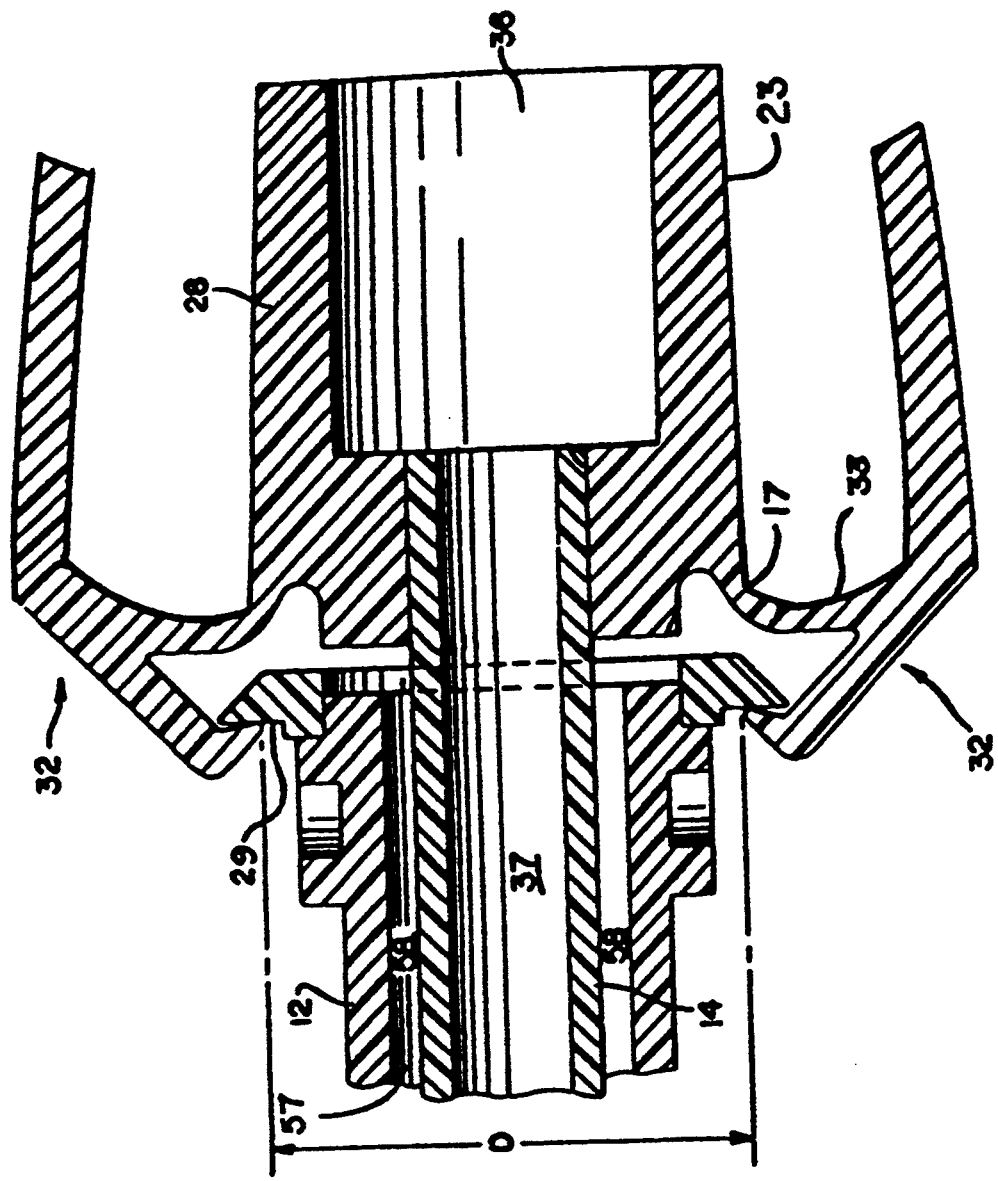
FIG. 3 is a cross sectional view of the latch, connector head, inner cannula, and outer cannula as viewed along the section line 3—3 of FIG. 2.

As depicted in FIG. 1, a typical tracheostomy tube assembly 10 comprises an inner cannula 14 and outer cannula 12. Cannulae 12, 14 are secured together via locking device 32. Locking device 32 prevents disconnection of cannulae 12, 14 by the patient. However, a care giver may easily disconnect locking device 32 with little or no discomfort to the patient.

With reference to FIGS. 1 and 3, outer cannula 12 is an arcuate, elbow-shaped tube, having a proximal end 18 and distal end 40. Outer cannula 12, contains a bore 58. Bore 58 has a diameter sufficient to accommodate inner cannula 14. In use, a care giver inserts distal end 40 into a patients airway through a puncture wound in the neck, while a portion of proximal end 18 remains outside the patient's neck.

As depicted in FIGS. 1, 2 and 3, inner cannula 14 has a proximal end 30 and a distal end 39. In a preferred embodiment, the inner cannula 14 is an arcuate, elbow-shaped tube having a flare towards the distal end 39. Inner cannula 14 contains a longitudinal bore 37, to provide a pathway for oxygen from a source outside the patient's body to the patient's lungs. Inner cannula 14 fits within outer cannula 12. Flared, distal end 39 of inner cannula 14 contacts inner bore surface 57 of outer cannula 12. This firmly secures distal ends 39, 40 of cannulae 12, 14 together.

Connector head 28 with a top 13 and base 15 is provided on the inner cannula 14. Base 15 provides a surface to which locking device 32 is either integrally formed or attached. In the preferred embodiment, base 15 is round, having a larger circumference than connector top 13 so that connector head 28 has a tapered configuration. In addition, the base 15 has a circumference larger than the circumference of bore 58 of outer cannula 12. Consequently, the larger circumference of base 15 prevents insertion of connector head 28 into bore 58 of outer cannula 12.

Top 13 of connector head 28 provides an attachment for an air source. The connector head has a longitudinal bore 36, for communication with bore 37 of inner cannula 14. Connector head bore 36 provides an air path via a connector 21 (see FIG. 5) from the ambient air, or a mechanical air source, to inner cannula 14.

Figure 5:
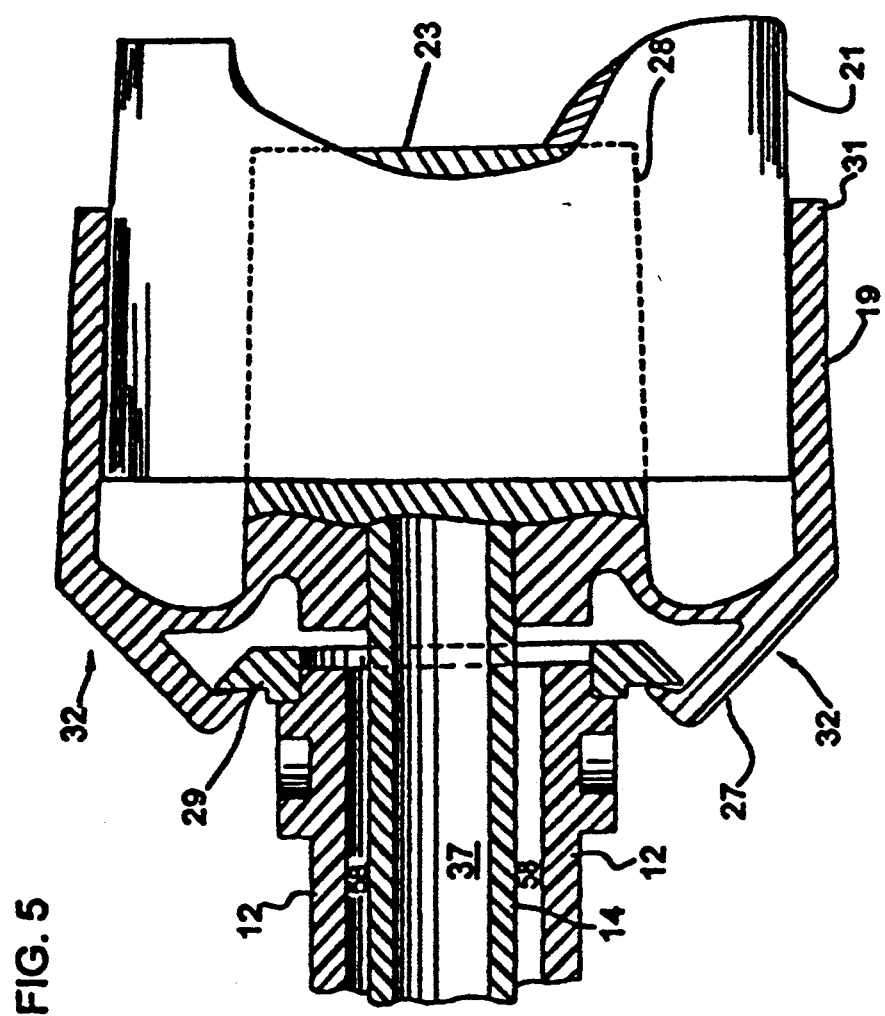
FIG. 5 is a side view, partially in section, of the view of FIG. 4, including a connector partially inserted on the connector head.

With reference to FIG. 5, a ventilator connector 21 is mated to connector head 28. Preferably, connector 21 has a longitudinal, tapered bore (not shown), adapted to mate with tapered connector head 28. An example of such a connector is an ISO (International Standards Organization) connector.

Cannulae 12, 14 are secured to each other via locking device 32. The locking device 32 attaches to inner cannula 14 at a rigid connection point 17. Locking device 32 contains at least one handle 19 and hook 27.

Handle 19, having a top 31 and bottom 38, is elongated such that it extends essentially normal from connection point 17 and essentially parallel to connector head 28. In proximity to handle top 31 is pressure point 34, where pressure is applied to open locking device 32. Because handle 19 is elongated, its pressure point 34 is spaced apart from the connection point 17 of the locking device 32.

Handle 19 is spaced from connector head 28. The distance from connector head 28 to handle 19 is essentially equal to the thickness of ventilator connector 21. The thickness is measured as the distance from outer wall 23 of connector head 28 to the nearest point on the outside surface of connector 21. A friction fit between the connector 21 and connector head 28 is achieved when connector 21 is inserted on the connector head 28.

When connector 21 is affixed to connector head 28, movement by handle 19 toward connector head 28 is limited. In addition, the length of handle 19 and the spatial relationship between handle 19 and connector 21 prevents overextension of handle 19 in a direction towards the connector head 28. In effect, connector 21 acts as a stop for handle 19.

A hook securing collar 29 which circumscribes outer cannula 12 is provided around and fixed to outer cannula 12. Collar 29 is preferably flared and facilitates connection with hook 27. When the inner cannula 14 is inserted into outer cannula 12, base 15 of connector head 28 abuts hook securing collar 29 and hook 27 grasps flared, hook securing collar 29.

Hook 27 extends from connection point 17 towards inner cannula 14 in a direction opposite of handle 19. When engaged, hook 27 contacts outer cannula 12 at flared collar 29. The contact of hook 27 around collar 29 secures outer cannula 12, thereby preventing movement of inner cannula 14 within outer cannula 12.

Locking device 32 has pivotal hinge 33. Hinge 33 allows movement of locking device 32 towards, and away from, connector head 28. In addition, hinge 33 provides resistance against movement. Consequently, locking device 32 returns to its original position when pressure is released from handle 19.

In the preferred embodiment, hinge 33 functions essentially as a fulcrum. Handle 19 and hook 27 pivot around hinge 33. Because handle 19 is spaced substantially from hinge 33, moving handle 19 against torque of hinge 33 and towards connector head 28 requires minimum effort. However, once pressure is released, locking device 32 returns to its original position.

To secure tube assembly 10 in place, an inflatable cuff 20 may be provided near distal end 40 of outer cannula 12. This cuff 20 inflates and contacts the trachea of the patient, wedging cannula 12 in place. In addition, a neck plate 24 may be provided. Neck plate 24 attaches to the outer cannula 12 at a position where cannula 12 exits the puncture wound. Attached to plate 24 is a band (not depicted). This band extends around the neck, and in concert with the neck plate 24, secures the tube 10 in place.

This device 10 may be constructed from a variety of plastic materials. However, it is preferred that the inner cannula 14 be constructed of flexible polyvinylchloride. In contrast, connector head 28 should be constructed of a more rigid material such as polypropylene. Other materials, such as polyethylene and polyoxymethylene, may be employed. The outer cannula 12 may be constructed of polyvinylchloride or polyurethane. The hook securing collar 29 may be constructed of rigid materials such as polysulfone, polycarbonate or polyetherimide.

Figure 4:
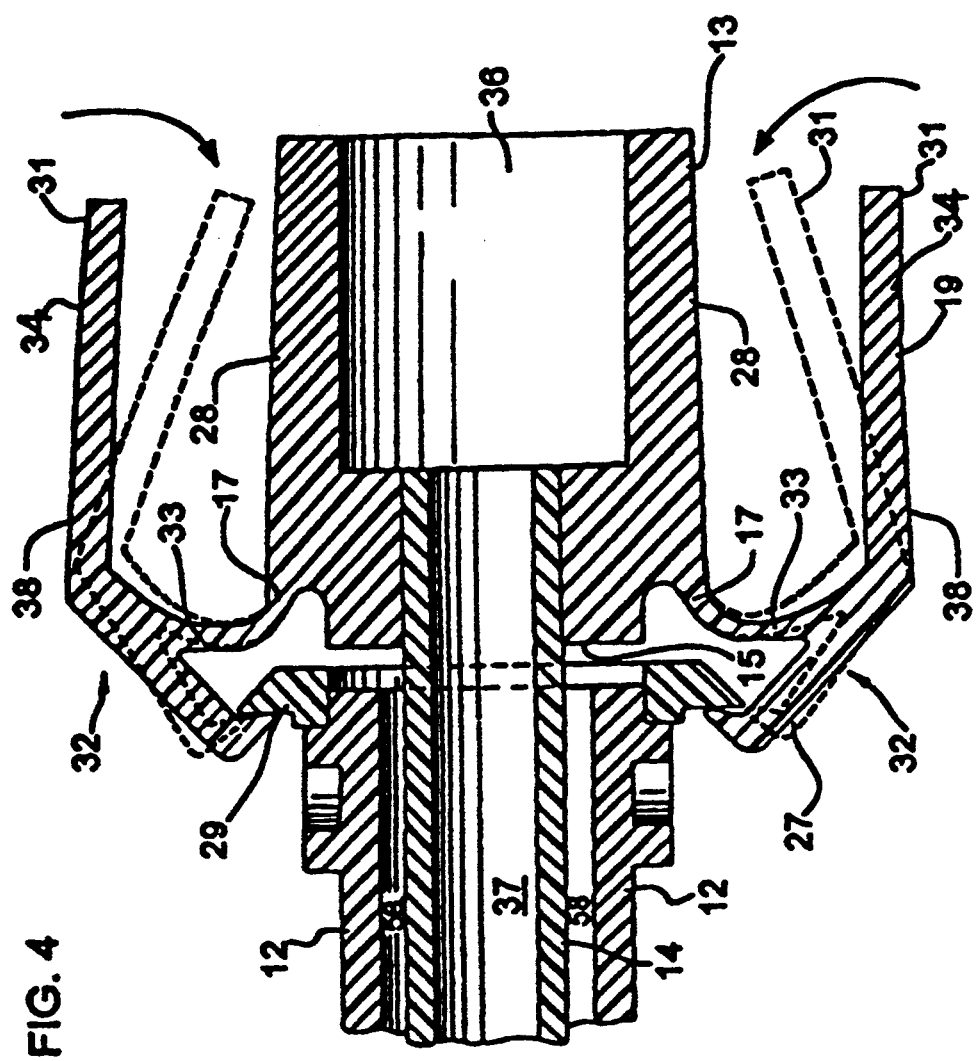
FIG. 4 is a side view, partially in section, of the inner cannula inserted into the outer cannula and the locking device, with the open position illustrated in phantom.

Having described the structure of the preferred embodiment, the process for connecting the tracheostomy tube assembly of the present invention can be understood with reference to FIGS. 2, 4, and 5. In general, the process involves connection of inner and outer cannulae 14, 12. Inner cannula 14 is inserted into outer cannula 12 and secured via use of locking device 32.

To begin the process, inner cannula 14 is inserted into outer cannula 12 until further insertion is prevented by locking device 32. Handle 19 is then compressed towards connector head 28. At this point, locking device 32 is in its open position, as depicted in phantom in FIG. 4.

Subsequently, inner cannula 14 is further inserted into outer cannula 12 until prevented by connector head 28 from further insertion. Pressure on handle 19 is then released and the resistance in hinge 33 returns locking device 32 to its original position, thereby clamping hook 37 around hook securing collar 29 and securing outer cannula 12 and inner cannula 14 together. The connector 21 may then be inserted on connector head 28, and the process in complete.

Although the description of the preferred embodiments has been quite specific, it is contemplated that various modifications may be made without deviating from the spirit of the present invention. Accordingly, it is intended that the scope of the present invention be dictated by the appended claims rather than by the description of the preferred embodiment.

What is claimed is:

1. A tracheostomy tube assembly comprising:
   an outer cannula and an inner cannula within the outer cannula;
   a connector head integrally formed with the inner cannula and adapted to mate with a connector;
   a readily detachable connector, having a longitudinal bore therethrough, attached to the connector head; and
   a locking device associated with the connector head and the inner cannula that holds the inner cannula securely to the outer cannula, the locking device including an elongated handle portion spaced apart from the connector head and pivotally connected to the inner cannula, and a hook portion extending in a direction opposite from the handle portion and pivotally connected to the inner cannula, such that movement of the handle portion is permitted towards, and away from, the inner cannula, and such movement moves the hook portion in the opposite direction;
   a space between the handle portion and the connector head which is sufficient for the connector to fit over the connector head so that when the connector is attached to the connector head the connector is between the handle portion and the connector head and the connector prevents movement of the handle portion;
   wherein the distance between the handle portion and the connector head is essentially equal to the thickness of the connector, as measured from an outer wall of the connector head to the nearest point on an outside surface of the connector such that when the connector is positioned on the connector head, the handle portion abuts the connector.

2. The device of claim 1 wherein the connector is a stop to prevent overextension of the handle portion.

3. The device of claim 1 wherein the connector head is tapered.

4. The device of claim 3 wherein the connector head and the connector meet ISO standards.

5. The device of claim 1 wherein the outer cannula has a hook engaging collar.

6. A tracheostomy tube assembly comprising:
   an outer cannula and an inner cannula within the outer cannula;
   a connector head integrally formed with the inner cannula and adapted to mate with a connector;
   a readily detachable connector, having a longitudinal bore therethrough, attached to the connector head; and
   a locking device associated with the connector head and the inner cannula that holds the inner cannula securely to the outer cannula, the locking device including an elongated handle portion spaced apart from the connector head and pivotally connected to the inner cannula, and a hook portion extending in a direction opposite from the handle portion and pivotally connected to the inner cannula, such that movement of the handle portion is permitted towards, and away from, the inner cannula, and such movement moves the hook portion in the opposite direction;
   a space between the handle portion and the connector head which is sufficient for the connector to fit over the connector head so that when the connector is attached to the connector head the connector is between the handle portion and the connector head and the connector prevents movement of the handle portion;
   wherein the distance between the handle portion and the connector head is sufficient to allow the connector to fit over the connector head but will not allow sufficient pivoting of the handle portion to allow inner cannula disconnection from the outer cannula when the connector is installed.

7. A method of assembling a tracheostomy tube assembly comprising:
   providing a disposable cannula with a connector head integrally formed with the disposable cannula; and with a locking device, the locking device having an elongated handle portion, pivotally connected to the disposable cannula; and the handle portion being separated from the connector head by a predetermined space;
   providing an outer cannula;
   inserting the disposable cannula into the outer cannula until movement is prevented by the locking device;
   compressing the handle portion of the locking device toward the connector head;
   inserting the disposable cannula until movement is prevented by the structure of the connector head;
   releasing pressure on the handle portion, thereby locking the disposable cannula to the outer cannula; and
   providing a connector having a bore therethrough for connection to the connector head, the connector having a thickness, as measured from an outer wall of the connector head to an inner wall of the connector, essentially equal to the predetermined space;
   inserting the connector on the connector head such that the handle portion abuts the connector and prevents further movement of the handle portion.

* * * * *